United States Patent
Kato (12)

(10) Patent No.: US 6,354,992 B1
(45) Date of Patent: Mar. 12, 2002

(54) AUTOMATED LAPAROSCOPIC LENS CLEANER

(76) Inventor: Daniel T. Kato, 1160 Carlos Privada, Mountain View, CA (US) 94040

( * ) Notice: Subject to any disclaimer, the term of this patent is extended or adjusted under 35 U.S.C. 154(b) by 0 days.

(21) Appl. No.: 09/435,566

(22) Filed: Nov. 8, 1999

(51) Int. Cl.$^7$ .............................................. A61B 1/015
(52) U.S. Cl. ......................... 600/157; 600/158; 600/159
(58) Field of Search ............................... 600/156, 157, 600/158, 159

(56) References Cited

U.S. PATENT DOCUMENTS

| 4,281,646 A |   | 8/1981  | Kinoshita ..................... 128/6 |
|-------------|---|---------|--------------------------------------|
| 4,408,598 A | * | 10/1983 | Ueda .............................. 128/4 |
| 4,973,311 A | * | 11/1990 | Iwakoshi et al. ............ 604/119 |
| 5,201,908 A | * | 4/1993  | Jones ............................. 128/4 |
| 5,207,213 A |   | 5/1993  | Auhll et al. .................. 128/6 |
| 5,313,934 A |   | 5/1994  | Wiita et al. .................. 128/4 |
| 5,400,767 A |   | 3/1995  | Murdoch ....................... 128/4 |
| 5,464,008 A |   | 11/1995 | Kim ........................... 600/157 |
| 5,575,756 A | * | 11/1996 | Karasawa et al. ........... 600/157 |
| 5,637,075 A | * | 6/1997  | Kikawada .................... 600/153 |

FOREIGN PATENT DOCUMENTS

WO          WO 92/20274        11/1992

* cited by examiner

*Primary Examiner*—Linda C. M. Dvorak
*Assistant Examiner*—Jocelyn Ram
(74) *Attorney, Agent, or Firm*—Rudolf O. Siegesmund

(57) ABSTRACT

An apparatus and method for cleaning the objective lens of a laparoscope, endoscope, or coeloscope during surgery and also removing the solution and debris during and after the cleaning. The result is obtained by using a rigid hollow split sheath for the scope. The split sheath has two separate channels. One channel is for irrigation and the cleaning fluid flows through this channel to be directed onto the lens. The other channel is for suction to remove the solution and debris during and after the cleaning. Control buttons located at the operator's end activate the irrigation and suction functions. The control buttons for irrigation and suction are fabricated into an existing valve type device which can regulate either of these functions. In addition, two ports, one for irrigation and one for suction emerge from the operator's end to connect to the appropriate tubing for irrigation and suction. A rubber ring device screws down at the operator's end allowing the surgeon to secure the sheath to the scope and prevent any leakage of the standard carbon dioxide gas used to distend the abdomen for operative laparoscopy in the patient.

12 Claims, 4 Drawing Sheets

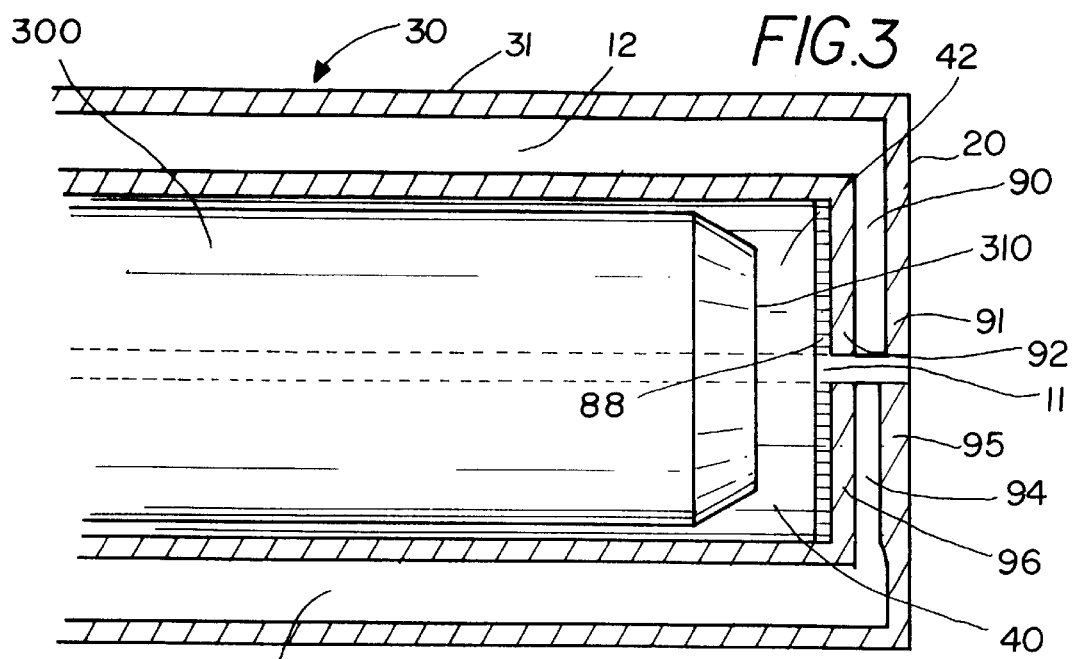
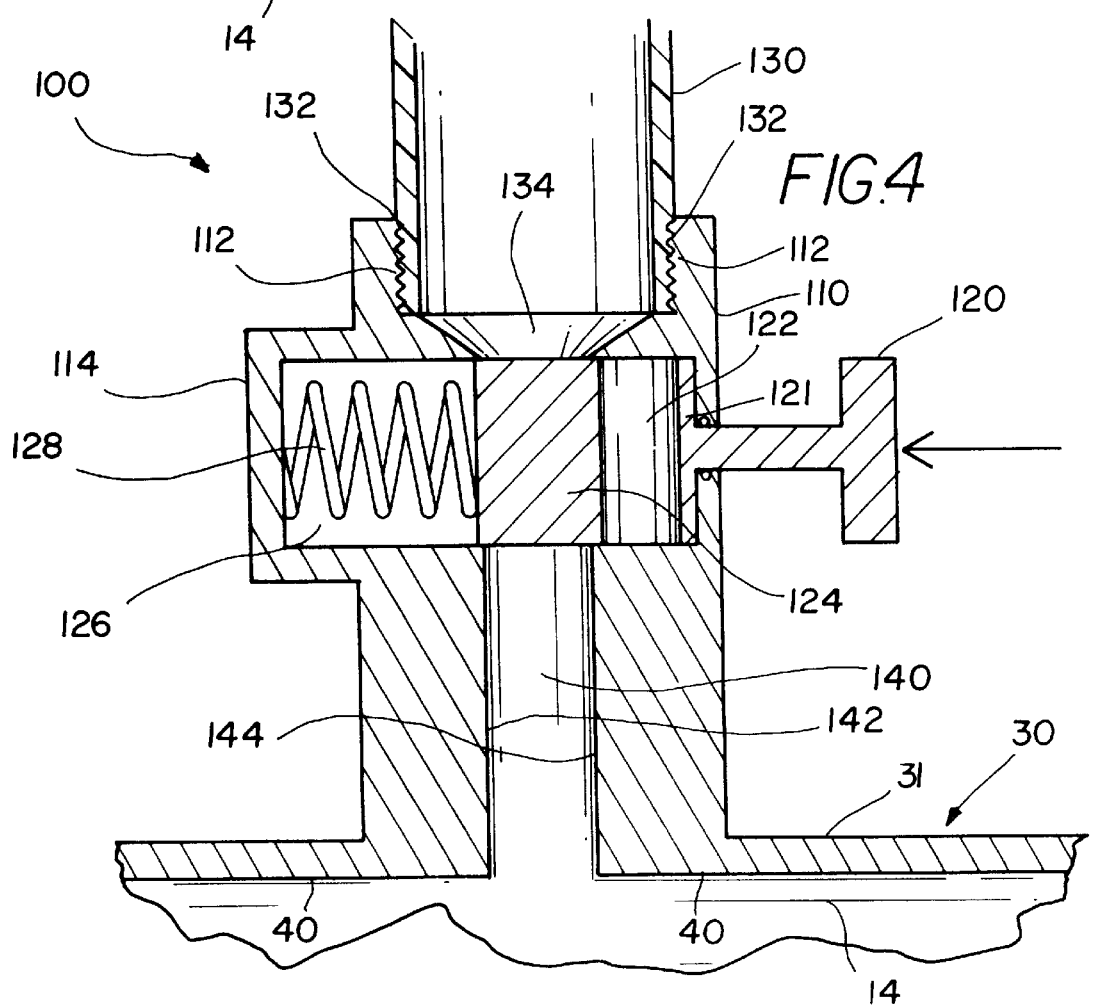

AUTOMATED LAPAROSCOPIC LENS CLEANER

BACKGROUND OF THE INVENTION

1. Field of the Invention

The present invention relates to an apparatus and method for cleaning and protecting the objective lens of a laparoscope, endoscope, or coeloscope. In particular, the invention relates to an apparatus and method for cleaning and protecting the objective lens of the laparoscope, endoscope or coeloscope while the scope is in use within a body cavity through an irrigation channel and suction channel within the apparatus.

2. Description of the Prior Art

Minimally invasive procedures, such as operative laparoscopy, have replaced simple and moderately complex surgical procedures that in the past have been done with large incisions, such as cholycystectomy, hysterectomy, and various gynecologic surgeries. Laparoscopic surgery is now recognized in most instances to substantially reduce patient care costs by decreasing post-operative patient discomfort and reducing hospitalization time. Ever more complex surgical procedures, such as intestinal resections, retroperitoneal lymph-node dissections, radical hysterectomy, spleenectomy, and nephrectomy for instance, are now being successfully accomplished by a laparoscopic surgical approach. Indeed, as longer and more complex surgical procedures are undertaken laparoscopically, laparoscopic surgeons rely on surgical techniques and novel laparasocopic instruments to facilitate laparoscopic surgery, reduce procedure time, and minimize the frustration which can be encountered when such techniques and instruments are not available.

As used herein, the term scope is meant to describe a laparoscope, endoscope, coeloscope or optical device used for observation within a body cavity and/or procedures being performed within a body cavity. Such scopes usually consist in part of a rigid or relatively rigid rod or shaft of approximately 300–500 mm length, with an outer diameter of 5 mm to 11 mm, having an objective lens at one end and an eyepiece at the other end. The rod or shaft of the scope contains light-transmitting glass fibres and/or rod lenses. In order to use such scopes, the body cavity must be illuminated with clear, bright light. Therefore, the scope also has a connection, adjacent to the eyepiece, for the attachment of an external light source which provides illumination, via light-transmitting fibres within the scope, of the features within the body cavity.

Prior to the introduction of the scope, the body cavity is normally inflated with a gas (usually carbon dioxide) using a gas insufflator. After the gas has been introduced, a plastic or metal sleeve or sheath, referred to as a trocar, is inserted through the wall of the cavity. The trocar contains a means for making a seal to prevent the leakage of gas from within the body cavity. The end of the scope containing the objective lens is inserted into the body cavity through the trocar. The attached light source is activated and the features within the body cavity are viewed, either directly through the eyepiece of scope, or on a video monitor receiving signals from a video camera attached to the eyepiece of the scope.

The objective lens of the scope often becomes soiled during operative procedures. Tissue particles, blood and other body fluids attach to the lens and obscure vision. When this happens, it is necessary to remove the scope from the body cavity and to clean the objective lens by wiping it with a suitable cloth. During some operative procedures, the scope may have to be removed frequently to wipe the lens clean.

Therefore, a need exists to clean the lens of the scope during surgery. Such devices are known in the art. U.S. Pat No. 4,281,646 to Kinoshita discloses a fluid passage extending through the sheath of a forward view type endoscope with a retractable nozzle for directing fluid onto the lens.

U.S. Pat. No. 5,313,934 to Wiita et. al. discloses a defined space within a sheath for passage of cleansing fluid. The cleansing fluid is directed by a discharge port onto the lens for cleansing and defogging.

U.S. Pat. No. 5,400,767 to Murdoch discloses a ridge near the end of the tube (sheath) where the ridge causes fluid injected into the tube to flow onto the lens. At the other end of the tube is means for making a seal to prevent leakage of air and/or fluid between the tube and the inserted shaft of the scope.

These prior art solutions introduce fluid onto the lens and into the body cavity. The fluids mix with the blood and tissue that are causing the problems. Therefore, a need exists for an apparatus and method for introducing cleansing fluid to the lens and also to remove the cleaning fluid and the blood and tissue which the cleansing fluid removed. It is to this need that the present invention is directed.

SUMMARY OF THE INVENTION

The present invention meets the needs and solves the problems identified above by providing an apparatus and method for cleaning the scope lens and also removing the solution and debris during and after the cleaning. The result is obtained by using a rigid hollow split sheath for the scope. The split sheath has two separate channels. One channel is for irrigation and the cleaning fluid flows through this channel to be directed onto the lens. The other channel is for suction to remove the solution and debris during and after the cleaning. Control buttons located at the operator's end activate the irrigation and suction functions. The control buttons for irrigation and suction are fabricated into an existing valve type device which can regulate either of these functions. In addition, two ports, one for irrigation and one for suction emerge from the operator's end to connect to the appropriate tubing for irrigation and suction. A rubber ring device screws down at the operator's end. The friction created by tightening down the ring device allows the surgeon to secure the sheath to the scope and prevent any leakage of pneumoperitoneum, i.e., leakage of the standard carbon dioxide gas used to distend the abdomen for operative laparoscopy in the patient. The operators end can be ergonomically designed so that a grip is attached to the sheath and the control buttons positioned for ease of one handed use.

The foregoing and other objects, features and advantages of the invention will be apparent from the following more particular description of a preferred embodiment of the invention, as illustrated in the accompanying drawings wherein like reference numbers represent like parts of the invention.

BRIEF DESCRIPTION OF THE DRAWINGS

in FIG. 1.

FIG. 3 is a cross-sectional view of the split sheath along line 3—3 in FIG. 1.

FIG. 4 is a cross-sectional view of the irrigation port along line 4—4 in FIG. 1.

DESCRIPTION OF PREFERRED EMBODIMENTS

Figure 1:
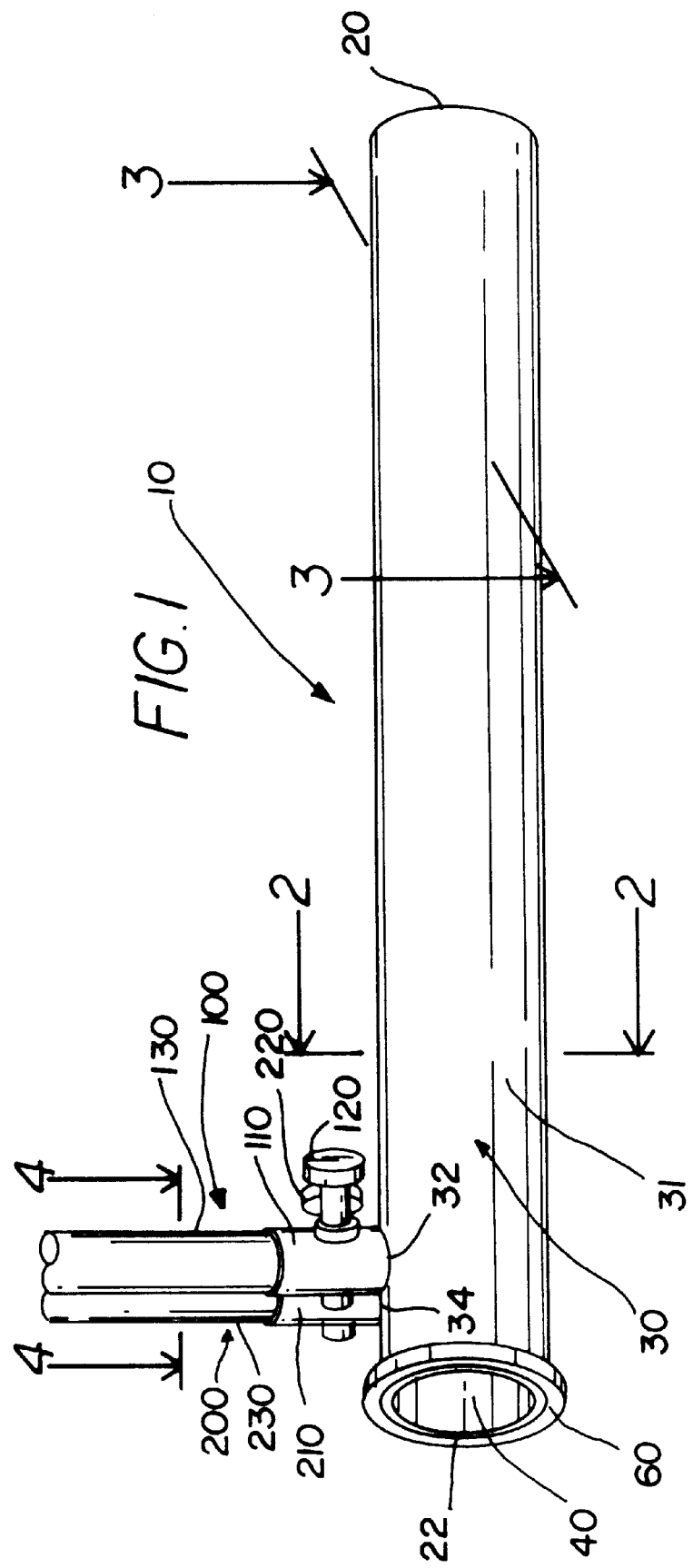
FIG. 1 is a side perspective view of the split sheath.

In FIG. 1, cleansing apparatus 10 is shown from a side perspective. Cleansing apparatus 10 has sheath 30, irrigation port 100 and suction port 200. Sheath 30 has patient end 20 and operator end 22. Operator end 22 of sheath 30 has ring 60 for tightening and sealing scope 300 (not shown in FIG. 1, see FIG. 3). Sheath 30 has outer surface 31 and inner surface 40. Irrigation port 100 has irrigation tubing 130, irrigation connector 110 and irrigation valve 120. Suction port 200 has suction tubing 230, suction connector 210 and suction valve 220. In FIG. 1, irrigation valve 120 and suction valve 220 are facing forward. The position of irrigation valve 120 and suction valve 220 can vary to meet the user's needs for comfort and accessibility. In the preferred embodiment, cleansing apparatus 10 is a disposable, one time use semi-automatic laparoscopic lens cleaning device fabricated from medical grade plastic. However, a laparoscope or other type of scope could be made in one piece employing the lens cleaning apparatus and method described herein. Irrigation tubing 130 may be standard, readily available flexible intravenous (IV) tubing, which is fed from a standard IV bag. Suction tubing 230 may be flexible tubing as is used in existing suction irrigator devices. It is possible that suction port 200 of cleansing apparatus 10 could run from the same pump as the suction irrigator used in surgery, thereby minimizing equipment and cost.

Figure 2:
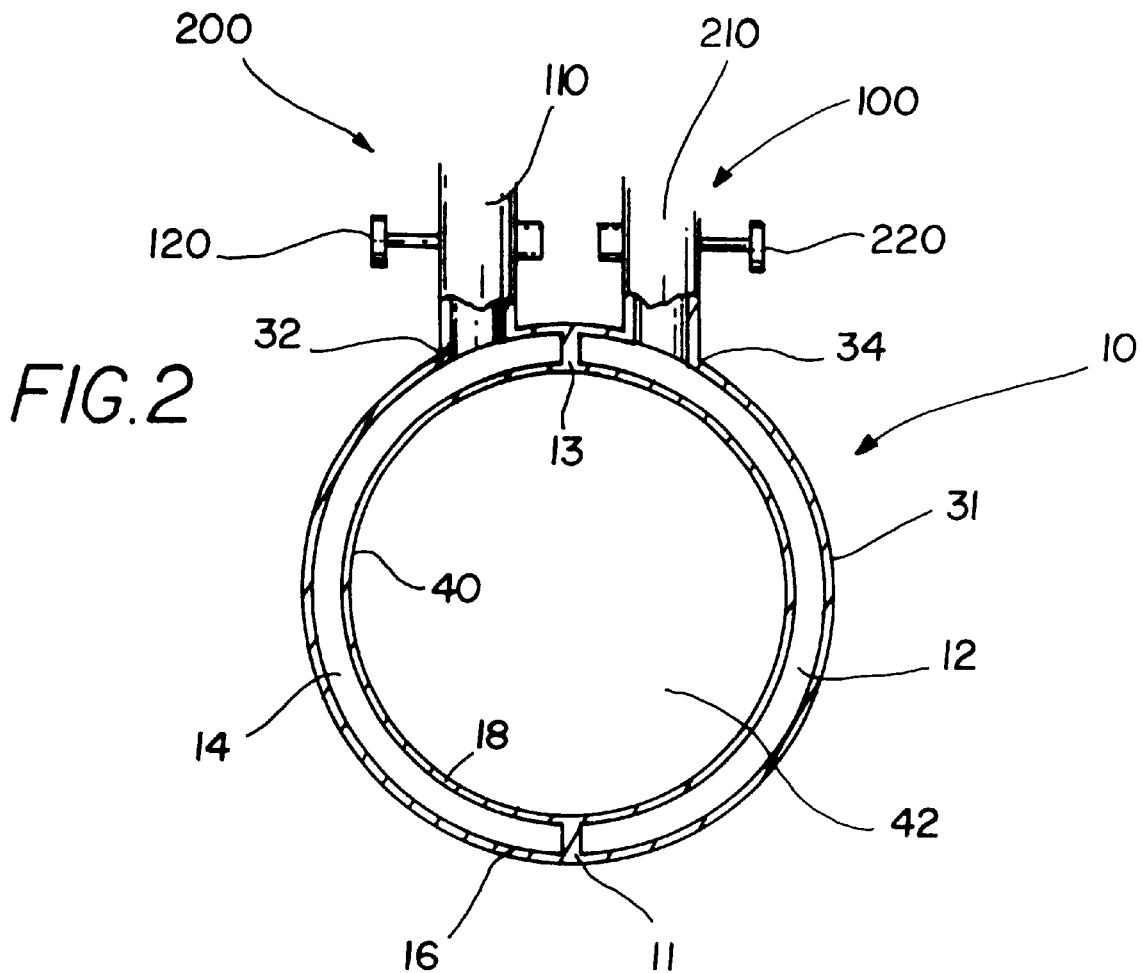
FIG. 2 is a cross sectional view of the split sheath along line 2—2.

FIG. 2 shows a cross section of sheath 30 along line 2—2 in FIG. 1. Sheath 30 has two defined interior spaces, irrigation channel 14 and suction channel 12 separated by top wall 13 and bottom wall 11. Sheath 30 has inner tube 18 and outer tube 16 connected by top wall 13 and bottom wall 11. Irrigation port 200 is connected to sheath 30 at irrigation entry point 32. Suction port 200 is connected to sheath 30 at suction entry point 34. Sheath 30 has outer surface 31 and inner surface 40. Inner surface 40 defines sheath inner cavity 42 for receiving scope 300 (not shown in FIG. 2, see FIG. 3). In FIG. 2, irrigation valve 120 and suction valve 220 are facing outward to show another embodiment from FIG. 1. The position of irrigation valve 120 and suction valve 220 can vary to meet the user's needs for comfort and accessibility.

FIG. 3 shows a cross sectional view of sheath 30 along line 3—3 in FIG. 1. Scope 300 is inserted into sheath inner cavity 42. Irrigation channel 14 extends the length of sheath 30 until irrigation channel 14 approaches patient end 20 of sheath 30. Inner tube 18 and outer tube 16 have inner tube patient end wall 94 and outer tube patient end wall 95 which extend at right angles to inner tube 18 and outer tube 16 until they are fixedly joined to bottom wall 11. Ridge 88 protrudes from inner tube 18 in order to stop forward movement of scope 300 toward patient end 20 of sheath 30. The distance ridge 88 protrudes from inner tube 18 will depend on the configuration of scope 300. Inner tube patient end wall 96 and outer tube patient end wall 95 and bottom wall 11 and top wall 13 (not shown) define irrigation nozzle 94 and suction nozzle 90 respectively. Irrigation nozzle 94 is shaped to direct fluid onto lens end 310 of scope 300 when scope 300 is seated against ridge 88.

FIG. 4. shows a cross sectional view of irrigation port 100 across line 4—4 of FIG. 1. Irrigation port 100 has irrigation connector 110 which is fixedly engaged to sheath 30. In the preferred embodiment, sheath 30, irrigation connector 110 and suction connector 210 are made from medical grade plastic and can be fashioned in one piece. Other embodiments could be manufactured using other materials such as lightweight metals. If irrigation connector 110 and suction connector 210 are not made from the same mold so that they are one piece, then irrigation connector 110 and suction connector 210 are attached to sheath 30 so that they are fixedly engaged and totally sealed. Irrigation connector 110 has irrigation connector extension 114 which contains irrigation housing cavity 126. Irrigation housing cavity 126 contains irrigation spring 128, irrigation seal block 124, irrigation pass block 122 and irrigation knob interior end 121. When an operator places manual pressure in the direction of irrigation connector 110 on irrigation knob 120 irrigation spring 128 is depressed allowing irrigation seal block 124 to move further into irrigation housing cavity 126 in the direction in which irrigation spring 128 is being depressed. As irrigation seal block 124 moves toward the compressed irrigation spring 128, irritation pass block 122 moves over irrigation port access cavity 140. Irrigation pass block 122 has a hollow aperture (not shown) which allows fluid to pass through irrigation pass block 122 from irrigation tube 130 and into irrigation port access cavity 140 which connects to irrigation channel 14. Irrigation tube 130 has first threads 132 for engaging second threads 112 in irrigation connector 110. Persons skilled in the art will be aware of many alternative ways to sealing engage irrigation tube 130 to irrigation connector 110. Irrigation tube 130 has irrigation tube tapered end 134 to facilitate control by irrigation seal block 124 and irrigation pass block 122.

Although not shown, suction port 200 functions in an identical manner to irrigation port 100 and all of the components are the same. Suction port 200 has suction connector (same as irrigation connectors 110) which is fixedly engaged to sheath 30. Suction connector (Same as irrigation connector 110) has suction connector extension (same as irrigation connector extension 114) which contains suction housing cavity (same as irrigation housing cavity 126). Suction housing cavity contains suction spring (same as irrigation spring 128), suction seal block (same as irrigation seal block 124), suction pass block (same as irrigation pass block 122) and suction knob interior end (same as irrigation knob interior end 121). When an operator places manual pressure in the direction of suction connector on suction knob, suction spring (same as irrigation spring 110) is depressed allowing suction seal block (same as irrigation seal block 124) to move further into suction housing cavity (same as irrigation housing cavity 126) in the direction in which suction spring is being depressed. As suction seal block moves toward compressed suction spring 128, suction pass block moves over suction port access cavity (same as irrigation port access cavity 140). Suction pass block has a hollow aperture which allows fluid to pass through suction pass block from suction tube 230 (See FIG. 2) and into suction port access cavity (same as irrigation port access cavity 140) which connects to suction channel 12 (See FIG. 2). Suction tube 230 has threads for engaging threads in suction connector 210 (See FIG. 2). Persons skilled in the art will be aware of many alternative ways to sealing engage suction tube 130 to suction connector 210. Suction tube 230 has suction tube tapered end (same as irrigation tube tapered end 134) to facilitate control by suction seal block and suction pass block.

Figure 5:
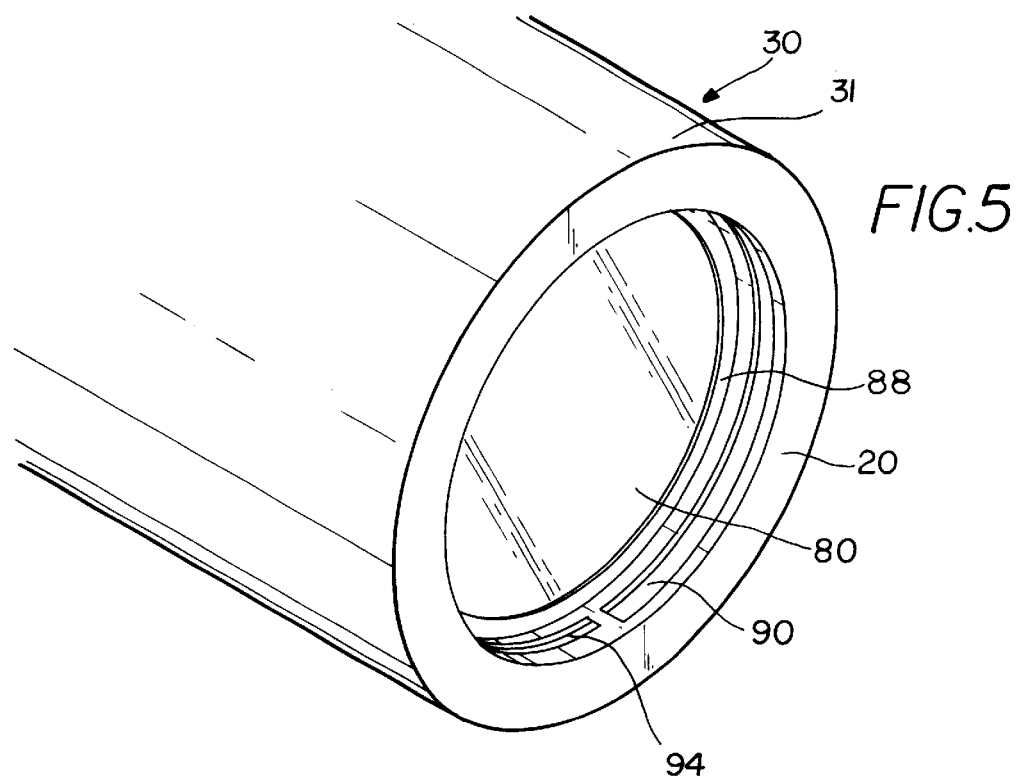
FIG. 5 is a partial perspective view of the patient end of the split sheath.
Figure 6:
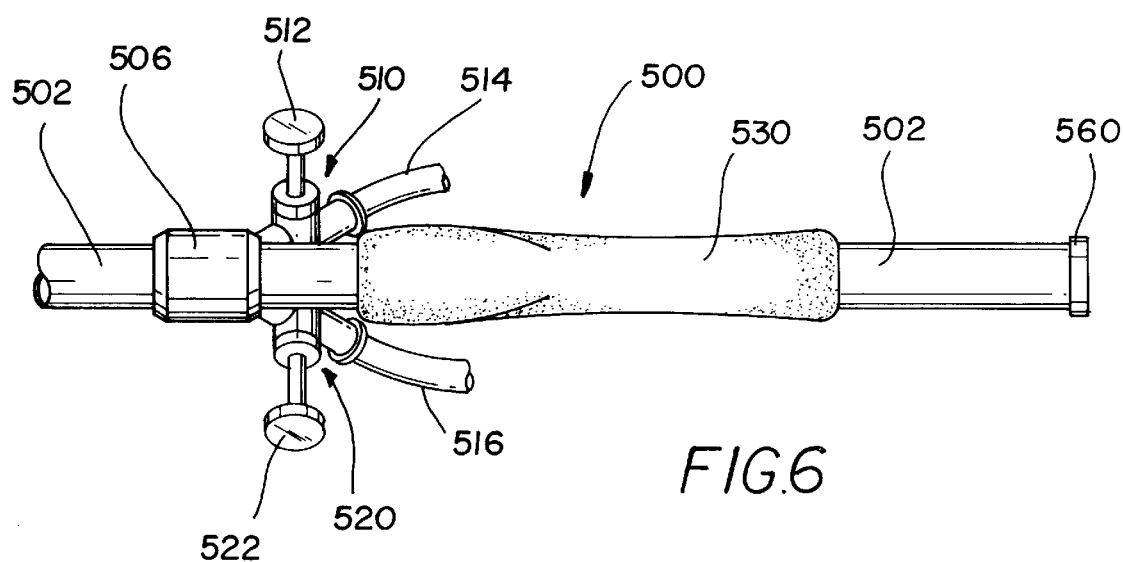
FIG. 6 is a perspective view of an ergonomic design for the sheath and irrigation and suction ports.

FIG. 5 depicts patient end 20 of sheath 30. Lens 80 of scope 300 (see FIG. 3) rests against ridge 88. Ridge 88 is positioned so as not to obscure optical viewing through lens 80, and to provide optimal fluid and suction vortex dynamics for the irrigation and suction functions to perform. Patient end 20 of sheath 30 extends slightly from lens 80 of scope 300 (see FIG. 3). Lens 80 is recessed slightly inside sheath 30 so that cleansing fluid is directed axially onto lens 80. Fluid may be directed onto lens 80 from irrigation nozzle 94 which is shaped to maximize the flow of cleansing fluid onto lens 80. The cleansing solution can be standard saline or sterile water which are readily available in all operating rooms. The cleansing solution can be warmed to reduce fog formation on lens 80. Suction nozzle 90, when activated will draw off the cleansing fluid and the blood, tissue or particles that are being cleaned from lens 80. More specifically, when suction knob 220 (See FIG. 2) is depressed, suction at suction nozzle 90 creates a localized suction and vortex effect, aspirating irrigation fluid and debris away from the surgical field. The amount of vacuum created can be controlled by the degree of pressure placed on suction knob 220. Suction nozzle 90 and irrigation nozzle 94 are honed or tailored to obtain the appropriate flow of irrigant and vortex needed to effectively rinse and clear lens 80. 510 and second suction port 520. Ergonomic connector 506 provides a means for attaching second irrigation port 510 and second suction port 520. Second irrigation knob 512 and second suction knob 522 are placed so that they can be easily operated with one hand while grasping handle 530. With scope 300 (see FIG. 3) secured within sheath 502, the surgeon has a comfortable, natural grip on cleansing apparatus 500 and a comfortable access to second irrigation knob 512 and second suction knob 522.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

I claim:

1. A laparoscopic lens cleaning device for encasing a laparoscopic lens comprising: an irrigation channel for selectively directing a cleansing fluid onto said laparoscopic lens; a suction channel for selectively removing said cleansing fluid and debris; wherein the laparoscopic lens cleaning device comprises a sheath having a length and a longitudinal axis, the sheath comprising two concentric tubes connected by a first wall and a second wall, the first wall and the second wall being parallel to the longitudinal axis along a majority of the length of the sheath, whereby the first wall and the second wall define the suction channel distinct from the irrigation channel.

2. The device of claim 1 further comprising:
   a suction port comprising:
      a suction tube connected to a suction pump and to the suction port;
      a knob fixedly and slidingly engaged to said suction port; and
      a housing cavity containing a spring, a seal block, a pass block and a knob interior end;
   wherein, when the knob is pushed toward the housing cavity, the knob interior end compresses the spring allowing the seal block to move toward the spring and the pass block to allow suction to flow from the suction tube to the suction channel.

3. The device of claim 1 further comprising:
   said suction channel having an operator end and a patient end; and
   said patient end further comprising a suction nozzle.

4. The device of claim 1 further comprising:
   a ring for sealing a scope in the laparoscopic lens cleaning device.

5. An apparatus for cleaning the objective lens of a scope during surgery comprising: a sheath having a length and a longitudinal axis for receiving said scope comprising a first side having an irrigation channel; a second side having a suction channel; an irrigation port fixedly engaged to said first side and selectively open to said irrigation channel, said irrigation port connected to a cleansing fluid container; and a suction port fixedly engaged to said second side and selectively open to said suction channel, said suction port connected to a suction pump, wherein the sheath comprises two concentric tubes connected by a first wall and a second wall, the first wall and the second wall being parallel to the longitudinal axis along a majority of the length of the sheath, whereby the first wall and the second wall define the first side distinct from the second side.

6. The apparatus of claim 5 further comprising: a suction nozzle in the first side; and an irrigation nozzle in the second side.

7. The suction port of claim 5 further comprising:
   a suction tube connected to the suction pump and to the suction port;
   a knob fixedly and slidingly engaged to said suction port; and
   a housing cavity containing a spring, a seal block, a pass block and a knob interior end;
   wherein, when the knob is pushed toward the housing cavity, the knob interior end compresses the spring allowing the seal block to move toward the spring and the pass block to allow suction to flow from the suction tube to the suction channel.

8. The irrigation port of claim 5 comprising:
   an irrigation tube connected to the cleansing fluid source and to the irrigation port;
   a knob fixedly and slidingly engaged to said irrigation port; and
   a housing cavity containing a spring, a seal block, a pass block and a knob interior end;
   wherein, when the knob is pushed toward the housing cavity, the knob interior end compresses the spring allowing the seal block to move toward the spring and the pass block to allow the cleansing fluid to flow from the irrigation tube to the irrigation channel.

9. A method for cleansing fluid and debris from an objective lens of a scope that is introduced into a body cavity through a trocar during surgery, comprising: selecting the trocar to have a sheath with a length and a longitudinal axis, the sheath comprising two concentric tubes connected by a first wall and a second wall, the first wall and the second wall being parallel to the longitudinal axis along a majority of the length of the sheath, whereby the first wall and the second wall define a suction channel distinct from an irrigation channel; directing a cleansing fluid onto the objective lens through the irrigation channel; and suctioning the cleansing fluid and debris away through the suction channel.

10. The method of claim 9, further comprising:
   introducing a cleansing apparatus into the trocar;
   connecting the cleansing apparatus to a suction pump and a source of cleansing fluid; and
   sealing the scope within the cleansing apparatus by tightening a ring.

11. The directing step of claim 10, further comprising:
   causing the cleansing fluid to flow through the irrigation channel by applying pressure to an irrigation knob.

12. The suctioning step of claim 10, further comprising:
   causing suction to flow through the suction channel by applying pressure to a suction knob.

* * * * *